United States Patent [19]

Anderson

[11] 4,047,105
[45] Sept. 6, 1977

[54] METHOD AND APPARATUS FOR PROVIDING AN OUTPUT INDICATION PROPORTIONAL TO THE MOISTURE CONTENT OF PARTICULATE MATERIAL

[75] Inventor: Bruce Olen Anderson, Oklahoma City, Okla.

[73] Assignee: The Dolese Company, Oklahoma City, Okla.

[21] Appl. No.: 660,917

[22] Filed: Feb. 24, 1976

[51] Int. Cl.² .................................. G01R 27/02
[52] U.S. Cl. .................................... 324/65 R
[58] Field of Search ............... 324/65 R, 65 P, 61 R

[56] References Cited
U.S. PATENT DOCUMENTS

| | | |
|---|---|---|
| 2,759,149 | 8/1956 | Hart .................................. 324/65 R |
| 3,141,129 | 7/1964 | Dietert .............................. 324/65 R |
| 3,631,337 | 12/1971 | MacKinney .................... 324/65 R |
| 3,896,373 | 7/1975 | Zelby ............................ 324/65 R X |
| 3,928,796 | 12/1975 | Kaiser .............................. 324/61 R |

Primary Examiner—Stanley T. Krawczewicz
Attorney, Agent, or Firm—Dunlap, Codding & McCarthy

[57] ABSTRACT

Method and apparatus for providing an output indication proportional to the moisture content of particulate material wherein a probe drive signal having predetermined frequency and amplitude is applied to the particulate material and a current indicator signal proportional to the current applied to the particulate material is provided, the current indicator signal being proportional to the moisture content of the particulate material.

12 Claims, 2 Drawing Figures

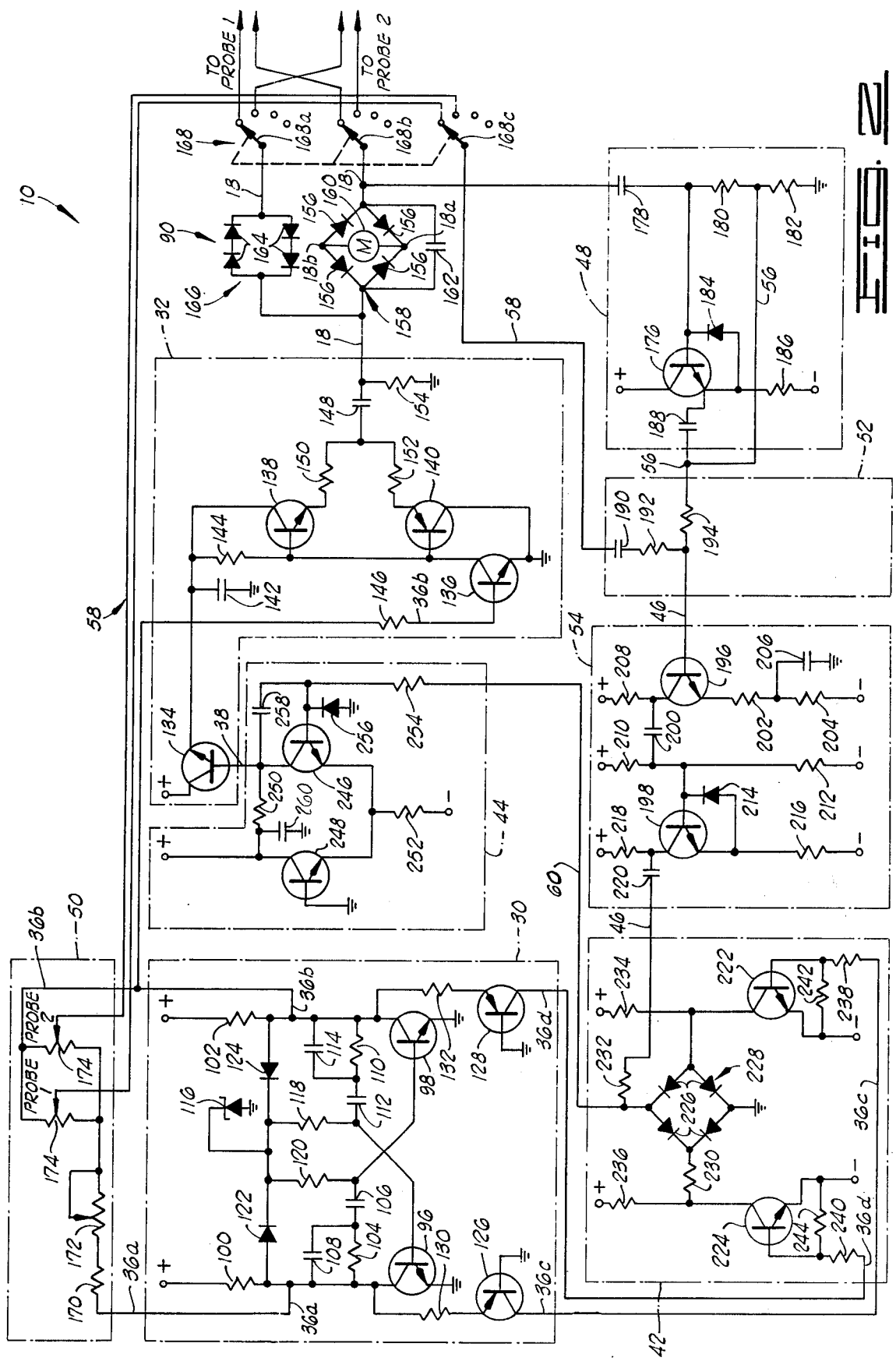

METHOD AND APPARATUS FOR PROVIDING AN OUTPUT INDICATION PROPORTIONAL TO THE MOISTURE CONTENT OF PARTICULATE MATERIAL

BACKGROUND OF THE INVENTION

1. Field of the Invention

This invention relates generally to a method and apparatus for providing an output indication proportional to the moisture content of particulate material and, more particularly, but not by way of limitation, to a method and apparatus for providing an output indication proportional to the moisture content of particulate material wherein a probe drive signal having predetermined frequency and amplitude is applied to the particulate material and a current indicator signal proportional to the current applied to the particulate material is provided, the current indicator signal being proportional to the moisture content of the particulate material.

2. Description of the Prior Art

In the past, various methods and apparatus have been devised to provide indications of the moisture content of particulate materials. Although such prior art devices are generally classifiable as either resistive or capacitive measuring devices, other methods for estimating the moisture content of materials have been devised such as the radio wave absorption device represented by the U.S. Pat. No. 3,714,560 issued to Farr. Representative of the capacitive measuring tape devices is the circuit disclosed in U.S. Pat. No. 3,300,716 issued to Engert.

Within the general catagory of resistive measuring devices, the prior art devices may be further subdivided according to the type of signal applied to the sample material, i.e., AC or DC. Within the DC subdivision are the prior art devices represented by the following U.S. patents: U.S. Pat. No. 2,548,410 issued to Tyson; U.S. Pat. No. 2,755,438 issued to Cudmore; and U.S. Pat. No. 3,197,699 issued to Johansen. Within the AC subdivision are the prior art devices represented by the following U.S. patents: U.S. Pat. No. 2,759,149 issued to Hart; and U.S. Pat. No. 3,141,129 issued to Dietert. The following U.S. patents disclose prior art devices of both the AC and DC types: U.S. Pat. No. 2,862,304 issued to Estienne; and U.S. Pat. No. 3,331,020 issued to Farenkopf.

Related prior art probe apparatus is disclosed in U.S. Pat. No. 3,631,337 issued to MacKinney.

SUMMARY OF THE INVENTION

The present invention contemplates a method and apparatus for providing output indications proportional to the moisture content of particulate material wherein a probe drive signal having predetermined frequency and amplitude is applied to the particulate material and a current indicator signal proportional to the current applied to the particulate material is provided, the current indicator signal being proportional to the moisture content of the particulate material.

It is an object of the present invention to provide an improved method for providing an output indication proportional to the moisture content of particulate material.

It is a further object of the present invention to provide an apparatus which effeciently applies the method of the present invention for providing an output indication proportional to the moisture content of particulate material.

Another object of the present invention is to provide a method for providing an output indication proportional to the moisture content of particulate material wherein a probe drive signal having predetermined frequency and amplitude is applied to the particulate material and a current indicator signal proportional to the current applied to the particulate material is provided, the current indicator signal being proportional to the moisture content of the particulate material.

Yet another object of the present invention is to provide an apparatus for efficiently applying the method of the present invention for providing an output indication proportional to the moisture content of particulate material, including means for generating a probe drive signal having predetermined frequency and amplitude, applying the probe drive signal to the particulate material, and providing a current indicator signal proportional to the current applied to the particulate material, the current indicator signal being proportional to the moisture content of the paticulate material.

Still another object of the present invention is to provide an apparatus for the character just described including means for maintaining the amplitude of the probe drive signal applied to the particulate material at the predeterined amplitude independently of the loading imposed on the probe drive signal.

Another object of the invention is to provide an improved probe which may be used advantageously with the method and apparatus of the present invention, the probe including means for isolating the flow of current from the probe to a predetermined portion of the particulate material thereby providing a more accurate output indication of the moisture content of the particulate material.

A still further object of the invention is to provide an apparatus for providing an output indication proportional to the moisture content of particulate material which is particularly easy to install and utilize but which is exceptionally stable and accurate in operation.

Yet another object of the present invention is to provide an apparatus for providing an output indication proportional to the moisture content of particulate material which is economical in construction and operation.

Other objects and advantages of the invention will be evident from the following detailed description when read in conjunction with the accompanying drawings which illustrate various embodiments of the invention.

BRIEF DESCRIPTION OF THE DRAWINGS

FIG. 2 illustrates in schematic form the preferred embodiment of the apparatus shown in diagrammatic form in FIG. 1.

DESCRIPTION OF THE PREFERRED EMBODIMENT

Figure 1:
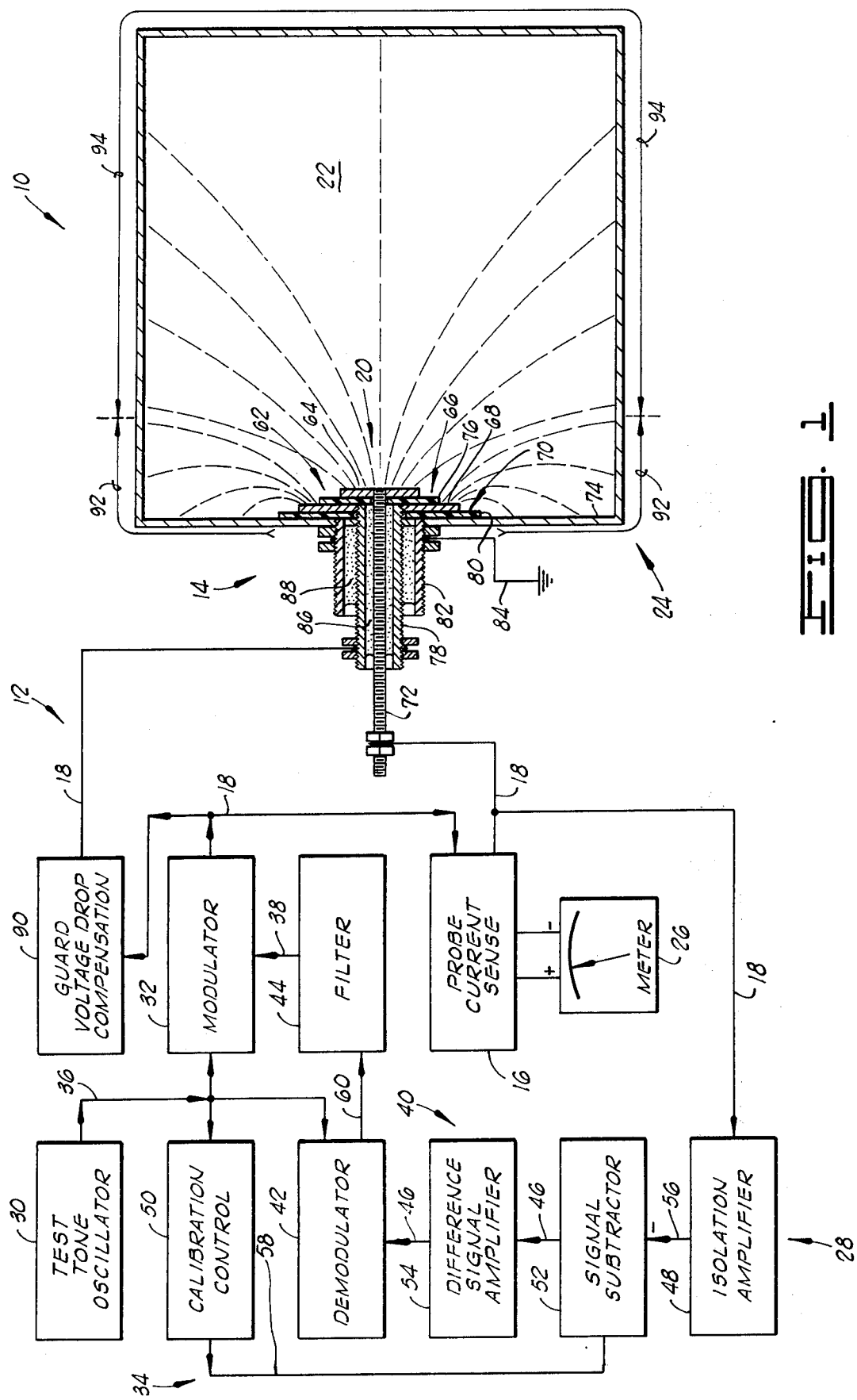
FIG. 1 illustrates in diagrammatical and partial sectional form an apparatus for providing output indications proportional to the moisture content of particulate material constructed in accordance with the present invention.

Referring to the drawings in general and to FIG. 1 in particular, shown therein and designated by the general reference number 10 is an apparatus for providing an output indication proportional to the moisture content of particulate material constructed in accordance with the preferred embodiment of the present invention. For convenience of reference, the apparatus shown in FIG. 1 will be referred to hereinafter simply as the moisture indicator 10.

The moisture indicator 10 is comprised generally of a signal generator 12, a probe 14, and a probe current sensor 16. The signal generator 12 is constructed to provide a probe drive signal having a predetermined frequency and a predetermined amplitude. The probe 14 is connected to the signal generator 12 via a general signal path 18 and has a portion 20 contacting a quantity of particulate material 22, which in the preferred embodiment is contained in a metal bin 24. The probe 14 is constructed to receive the probe drive signal provided by the signal generator 12 and apply the received probe drive signal to the particulate material 22. The probe current sensor 16, which is interposed in the signal path 18 generally between the signal generator 12 and the probe 14, is constructed to measure the current flowing from the probe 14 to the particulate material 22 and provide a current indicator signal via an ammeter 26 which is proportional to the measured current. As will be clear to those skilled in the art, the amount of current flowing from the probe 14 to the particulate material 22 will be proportional to the conductivity of the particulate material 22 which is in turn dependent upon the moisture content of the particulate material 22, so that the current indicator signal provided by the probe current sensor 16 will be proportional to the moisture content of the particulate material 22.

It has been discovered by the Applicant that the ability of a moisture indicating system, such as the moisture indicator 10, to provide an accurate output indication of the moisture content of particulate material is highly dependent upon the quality of the signal applied to the particulate material. It has been determined that it is preferable to apply an AC signal to the particulate material rather than a DC signal in order to avoid any error induced by any chemical activity occurring within the particulate material. It has been further determined that the amplitude of the signal applied to the particulate material should be maintained at a predetermined amplitude so that the output indication will be substantially independent of the load imposed on the moisture indicator 10 by the particulate material. To this end, the signal generator 12 of the moisture indicator 10 includes a feedback control circuit 28 which senses deviations of the probe drive signal applied to the particulate material 22 from the desired predetermined amplitude and modulates the amplitude of the probe drive signal being applied to the particulate material 22 to automatically compensate for the load imposed by the particulate material 22. An additional benefit gained by the use of the feedback control circuit 28 is the independence of the amplitude of the probe drive signal from any fluctuations in the power level supplied to the moisture indicator 10.

The signal generator 12 is comprised generally of a test tone oscillator 30, a modulator 32, and a probe command signal generator 34. The test tone oscillator 30 is constructed to provide a test tone signal via a general signal path 36, the test tone signal having the predetermined frequency which is preferably from 500Hz to 10KHz.

The modulator 32 is connected to receive the test tone signal provided by the test tone oscillator 30 via the signal path 36. The modulator 32 is also connected to receive a probe command signal provided by the probe command signal generator 34 via a general signal path 38 in a manner to be described in greater detail below. The modulator 32 modulates the amplitude of the received test tone signal in response to the received probe command signal to provide the probe drive signal via the signal path 18.

The probe command signal generator 34 is connected to receive the test tone signal provided by the test tone oscillator 30 via the signal path 36. The probe command signal generator 34 also receives the probe drive signal from the probe 14 via the signal path 18. The probe command signal generator 34 provides the probe command signal via the signal path 38, the amplitude of which is proportional to the amplitude deviation of the received probe drive signal from the desired predetermined amplitude.

In the preferred embodiment, the probe command signal generator 34 is generally comprised of a subtractor 40, a demodulator 42, and a filter 44. The subtractor 40 is connected to receive the test tone signal provided by the test tone oscillator 30 via the signal path 36. The subtractor 40 is also connected to receive the probe drive signal from the probe 14 via the signal path 18. The subtactor 40 provides a difference signal via a general signal path 46, the amplitude of which is proportional to the amplitude deviation of the received probe drive signal from the desired predetermined amplitude.

More particularly, the subtractor 40 is comprised of an isolation amplifier 48, a calibration assembly 50, a signal subtractor 52, and a difference signal amplifier 54. The isolation amplifier 48 is connected to receive the probe drive signal from the probe 14 via the signal path 18 and provide a probe drive sense signal via a general signal path 56, the amplitude of which is proportional to the amplitude of the received probe drive signal. The calibration assembly 50 is connected to receive the test tone signal from the test tone oscillator 30 via the signal path 36 and provide a reference signal via a general signal path 58, the amplitude of which is proportional to the amplitude of the received test tone signal. As will be made more apparent below, the amplitude of the reference signal determines the predetermined amplitude of the probe drive signal. The signal subtractor 52 is connected to receive the probe drive sense signal from the isolation amplifier 48 via the signal path 56, and the reference signal from the calibration assembly 50 via the signal path 58; and subtract the received probe drive sense signal from the received reference signal to provide the difference signal via the signal path 46. The difference signal amplifier 54 is interposed in the signal path 46 to increase the amplitude of the difference signal for application to the demodulator 42.

The demodulator 42 is connected to receive the difference signal from the subtractor 40 via the signal path 46. The demodulator 42 is also connected to receive the test tone signal from the test tone oscillator 30 via the signal path 36. The demodulator 42 demodulates the received difference signal to derive the portion of the received difference signal which is in phase with the received test tone signal for output as a demodulated difference signal via a general signal path 60.

The filter 44 is connected to receive the demodulated difference signal from the demodulator 42 via the signal path 60. The filter 44 filters the received demodulated difference signal to provide the probe command signal via the signal path 38.

In addition to the importance of the quality of the signal applied to the particulate material, it has been discovered by the Applicant that the accuracy of a moisture indicating system, such as the moisture indicator 10, improves significantly as the proportion of the particulate material effectively sampled by the probe drive signal is increased relative to the total quantity of particulate material. It has been determined that the AC signal applied by the moisture indicator 10 to the particulate material 22 exhibits a significant tendency to flow between the probe 14 and the relatively near portions of the bin 24 through the intervening particulate material 22. The cummulative effect of such a tendency is to effectively limit the proportion of the particulate material measured by the moisture indicator 10 to a relatively small proportion of the overall quantity of particulate material 22. Thus it is preferable to isolate the probe 14 from the relatively near portions of the bin 24 so as to force the current provided by the moisture indicator 10 to flow between the probe 14 and the relatively far portions of the bin 24, thereby increasing the effective sample size of the moisture indicator 10. To this end, the probe 14 of the moisture indicator 10 includes an isolation assembly 62, which isolates the measured flow of current provided by the probe 14 to the portion of the particulate material 22 lying between the probe 14 and the relatively far portions of the bin 24.

In the preferred embodiment, the probe 14 is comprised generally of a measurement contact 64, a measurement contact insulator 66, a guard contact 68 and a guard contact insulator 70. The measurement contact 64 is positioned inside the bin 24 with at least a portion of the measurement contact 64 contacting the particulate material 22. The measurement contact 64 is mounted on the end of a measurement contact lead 72 which passes through and is retained by a portion of the wall 74 forming the bin 24. The measurement contact 64 is connected to the signal generator 12 via the signal path 18 and the measurement contact lead 72 connected therebetween. The measurement contact insulator 66 has a first portion 76 interposed between the measurement contact 64 and the adjacent portion of the bin 24 to prevent the direct flow of current between the measurement contact 64 and the adjacent portion of the bin 24.

The guard contact 68 is interposed generally between the measurement contact insulator 66 and the adjacent portion of the bin 24 with at least a portion of the guard contact 68 contacting the particulate material 22. The guard contact 68 is mounted on the end of a substantially cylindrical guard contact lead 78 which is coaxial with the measurement contact lead 72 and also passes through and is supported by the wall 74 of the bin 24. The guard contact 68 is connected to the signal generator 12 via the general signal path 18 and the guard contact lead 78 connected therebetween. The guard contact insulator 70 has a first portion 80 interposed generally between the guard contact 68 and the adjacent portion of the bin 24 to prevent the direct flow of current between the guard contact 68 and the adjacent portion of the bin 24.

The bin 24 has a substantially cylindrical bin ground lead 82 connected thereto so as to be substantially coaxial with the measurement contact lead 72 and the guard contact lead 78. The bin ground contact 82 is connected to the ground of the moisture indicator 10 via a signal path 84 for reasons which will be made more apparent below. The measurement contact insulator 66 has a second portion 86 interposed generally between the measurement contact lead 72 and the guard contact lead 78 to prevent the direct flow of current between the measurement contact lead 72 and the guard contact lead 78. The guard contact insulator 70 has a second portion 88 interposed generally between the guard contact lead 78 and the bin ground lead 82 to prevent the direct flow of current between the guard contact lead 78 and the bin ground lead 82.

In the preferred embodiment, a guard voltage drop compensation assembly 90 is interposed in signal the path 18 generally between the signal generator 12 and the guard contact 68 to compensate for any voltage drop induced by the probe current sensor 16 in the probe drive signal passing therethrough. Thus the amplitude of the signal being applied to the particulate material 22 via the guard contact 68 will be substantially equal to the amplitude of the signal being applied to the particulate material 22 via the measurement contact 64. The cummulative effect of having substantially equivalent signals applied to each of the measurement and guard contacts 64 and 68, respectively, is to effectively isolate the flow of current from the guard contact 68 to the portion of the particulate material 22 lying between the guard contact 68 and the portion of the bin 24 (referred to in FIG. 1 by the reference number 92), while isolating the flow of current from the measurement contact 64 to the remaining portion of the particulate material 22 lying between the measurement contact 64 and the remaining portion of the bin 24 (referred to in FIG. 1 by the reference number 94). In other words, the guard contact 68 forces the measurement contact 64 to sample a much larger proportion of the particulate material 22 contained within the bin 24 than would otherwise be sampled.

EMBODIMENT OF FIG. 2

Shown in FIG. 2 is a moisture indicator 10 constructed to operate in accordance with the preferred embodiment shown in FIG. 1 and described generally above. It is to be understood hereinafter that the operational elements comprising the moisture indicator 10 as shown in FIG. 2 are to be powered by a stable DC power source providing a positive operating potential, a negative operating potential, and a circuit ground centered between the positive and negative operating potentials. Although the moisture indicator 10 shown in diagrammatical form in FIG. 1 was described as being generally applicable to a single bin 24, the moisture indicator 10 shown in schematic form in FIG. 2 has appropriate modifications included therein to clearly demonstrate the ease with which the moisture indicator 10 may be adapted to provide output indications of the moisture content of particulate materials contained in a plurality of bins.

The test tone oscillator 30 is comprised generally of a pair of transistors 96 and 98 connected to form an astable multivibrator the output of which is taken from the collectors of the transistors 96 and 98. The emitters of the transistors 96 and 98 are each connected to the circuit ground while the collectors thereof are connected to the positive operating potential via the load resistors 100 and 102, respectively. The collector of the transistor 96 is connected to the base of the transistor 98 via a resistor 104 and a capacitor 106, with a capacitor 108 being connected in parallel with the resistor 104. The collector of the transistor 98 is connected to the base of the transistor 96 via a resistor 110 and a capacitor 112, with a capacitor 114 being connected in parallel with the resistor 110. The base of the transistor 96 is also connected to the cathode of a zener diode 116 via a resistor 118 and the base of the transistor 98 is also connected to the cathode of the zener diode 116 via a resistor 120, the anode of the zener diode 116 being connected to the circuit ground. The cathodes of a pair of diodes 122 and 124 are also connected to the cathode of the zener diode 116, while the anodes thereof are connected to the collectors of the transistors 96 and 98, respectively.

As will be clear to those skilled in the art, the test tone oscillator 30 will operate as an astable multivibrator upon being supplied with operating power. The substantially square-wave AC signal produced by the test tone oscillator 30 at the collectors of the transistors 96 and 98 are made available for use by the moisture indicator 10 via the signal paths 36a and 36b. As will be clear to those skilled in the art, the test tone signal on the signal path 36a will be substantially 180° out of phase with the test tone signal of the signal path 18b.

In the preferred embodiment, the test tone oscillator 30 also includes a pair of amplifying transistors 126 and 128, the emitters of which are connected to the collectors of the transistors 96 and 98, respectively, via resistors 130 and 132, respectively. The bases of the amplifying transistors 126 and 128 are each connected to the circuit ground, while the collectors thereof are connected to the signal paths 36c and 36d, respectively. As will be clear to those skilled in the art, the amplifying transistors 126 and 128 operate to shift the test tone signal in amplitude and DC reference level for use by the demodulator 42.

The modulator 32 is comprised generally of an amplitude control transistor 134, a chopper transistor 136, and a pair of output transistors 138 and 140. The amplitude control transistor 134 has the collector thereof connected to the positive operating potential, the emitter thereof connected to the collector of the output transistor 138, and the base thereof connected to the filter 44 via the signal path 38. A capacitor 142 is interposed between the emitter of the amplitude control transistor 134 and the system ground to smooth the output from the amplitude control transistor 134. A resistor 144 connects the emitter of the amplitude control transistor 134 to the base of the output transistor 138, the base of the output transistor 140, and the collector of the chopper transistor 136. The base of the chopper transistor 136 is connected to the test tone oscillator 30 via the signal path 36b and a resistor 146. The emitter of the chopper transistor 136 and the collector of the output transistor 140 are each connected to the circuit ground. The emitter of the output transistor 138 is connected to one side of a capacitor 148 via a resistor 150 and the emitter of the output transistor 140 is also connected to the same side of the capacitor 148 via a resistor 152. The other side of the capacitor 148 is connected to the signal path 18 and to the circuit ground via a resistor 154.

The probe current sensor 16 consists generally of a set of four diodes 156 connected to form a conventional rectifier 158, the AC input terminals of which are connected in series with the signal path 18. The positive DC output terminal of the rectifier 158 is connected to the positive input terminal of a conventional ammeter 160 via the signal path 18a. The negative DC output terminal of the rectifier 158 is connected to the negative input terminal of the ammeter 160 via the signal path 18b. In addition, a capacitor 162 is connected across the AC input terminals of the rectifier 158. As will be clear to those skilled in the art, any current flowing through the signal path 18 will be diverted by the rectifier 158 through the ammeter 160 and thereby produce a visually perceivable output indication proportional to the current flowing through the signal path 18.

The guard voltage drop compensation assembly 90 consists of a set of four diodes 164 connected to substantially form a conventional rectifier 166, with the AC input terminals thereof connected in series with the signal path 18.

As explained generally above, the moisture indicator 10 shown in FIG. 2 has been adapted to provide output indications of the moisture content of particulate material contained in a plurality of bins. For this reasons, a triple pole, multi-throw switch assembly 168 has been provided with one pole 168a interposed in signal path 18 between the guard voltage drop compensation assembly 90 and the guard contacts 68 of a pair of probes 14 (referred to in FIG. 1 as "Probe 1" and "Probe 2"), and a second pole 168b interposed in the signal path 18 between the probe current sensor 16 and the measurement contact 64 of the respective probes 14.

The calibration control 50 consists of a fixed trim resistor 170 and a variable trim resistor 172 connected in series with the signal path 36a, and a plurality of calibration resistors 174, there being one calibration resistor 174 for each of the probes 14 connected to the moisture indicator 10 as explained above. As will be clear to those skilled in the art, the fixed trim resistor 170 and the variable trim resistor 172 cooperate to maximize the effectiveness of the calibration resistors 174. The calibration resistors 174 in turn enable the amplitude of the reference signal being fed to the signal subtractor 52 via the signal path 58 to be adjusted to compensate for differences in the physical and chemical characteristics of a particular batch of particulate material 22. In the preferred embodiment, the reference signal being provided by the calibration control 50 is connected through a third pole 168c of the switch assembly 168 to the signal subtractor 52.

The isolation amplifier 48 consists primarily of a buffer transistor 176, the base of which is connected to the calibration assembly 50 via the signal path 18 and a coupling capacitor 178. The base of the buffer transistor 176 is also connected to the circuit ground via a pair of resistors 180 and 182, and to the emitter thereof via a protecting diode 184. The emitter of the buffer transistor 176 is also connected to the negative operating potential via a resistor 186 and to the signal path 56 via a coupling capacitor 188. The collector of the buffer transistor 176 is connected to the positive operating potential. The signal path 56 is also connected to the junction between the resistors 180 and 182.

The signal subtractor 52 consists of a capacitor 190 and a resistor 192 which are connected in series between the signal path 58 and the signal path 46, and a resistor 194 connected between the signal path 56 and the signal path 46.

The difference signal amplifier 54 consists primarily of a pair of amplifying transistors 196 and 198, the base of the amplifying transistor 196 being connected to the signal path 46, and the base of the amplifying transistor 198 being coupled to the collector of the amplifying transistor 196 via a capacitor 200. The emitter of the amplifying transistor 196 is connected to the negative operating potential via a pair of resistors 202 and 204, with a capacitor 206 being interposed between the junction between the resistors 202 and 204 and the circuit ground. The collector of the amplifying transistor 196 is connected to the positive operating potential via a resistor 208. The base of the amplifying transistor 198 is also connected to the positive operating potential via a resistor 210 and to the negative operating potential via a resistor 212. The emitter of the amplifying transistor 198 is connected to the base thereof via a protective diode 214 and to the negative operating potential via a resistor 216. The collector of the amplifying transistor 198 is connected to the positive operating potential via a resistor 218 and is coupled to the signal path 46 via a coupling capacitor 220.

The demodulator 42 consists primarily of a pair of transistors 222 and 224, and a set of four diodes 226 connected to substantially form a conventional rectifier 228 with the negative DC terminal being connected to the collector of the transistor 222 and the positive DC terminal being connected to the collector of the transistor 224 via a resistor 230. One of the AC terminals of the rectifier is connected to the signal path 46 via a resistor 232 and to the signal path 60, and the other AC terminal is connected to the circuit ground. The collector of the transistor 222 is also connected to the positive operating potential via a resistor 234 and the collector of the transistor 224 is also connected to the positive operating potential via a resistor 236. The base of the transistor 222 is connected to the collector of the transistor 126 via the signal path 36c and a resistor 238, while the base of the transistor 224 is connected to the collector of the transistor 128 via the signal path 36d and a resistor 240. The emitters of the transistors 222 and 224 are each connected to the negative operating potential, while the bases thereof are each connected to the negative operating potential via resistors 242 and 244, respectively.

The filter 44 consists primarily of a pair of transistors 246 and 248, the collectors of which are connected via a resistor 250, and the emitters of which are each connected to the negative operating potential via a common resistor 252. The base of the transistor 246 is connected to the signal path 60 via a resistor 254, to the circuit ground via a protective diode 256, and to the collector thereof via an integrating capacitor 258. The base of the transistor 248 is connected to the circuit ground. The collector of the transistor 248 is also connected to the positive operating potential and to the circuit ground via a bypass capacitor 260, while the collector of the transistor 246 is connected to the signal path 38.

OPERATION OF THE PREFERRED EMBODIMENT

It will be assumed hereinafter that the meter movement of the ammeter 160 has been mechanically zeroed, that the positive and negative operating potentials have been connected as shown in FIG. 2 and that the switch assembly 168 has been positioned as also shown in FIG. 2.

To calibrate the mositure indicator 10, the signal paths 18 should be disconnected from the probes 14, the calibration resistors 174 should be positioned so as to connect the signal paths 58 directly to the variable trim resistor 172, and the variable trim resistor 172 adjusted to provide an AC amplitude of 0 volts on the signal path 18. Thereafter, the signal paths 18 may be reconnected to the probes 14 and a quantity of particulate material 22 to be measured disposed in the bin 24 in contact with the probe 14 (Probe 1). A representative sample of the particulate material 22 contained in the bin 24 should then be taken and the mositure content thereof determined by conventional means. The calibration resistor 174 associated with the probe 14 may then be adjusted so that the output indication provided by the ammeter 160 substantially corresponds to the mositure content of the particulate material 22 as determined by the conventional means. Thereafter, any other calibration resistors 174 may each be adjusted to provide calibrated output indications for each of the bins 24 of particulate material 22 in which the respective probes 14 are installed. In this manner, each of the probes 14 may be independently calibrated to provide accurate output indications of the moisture content of the particulate material 22 disposed in the bin 24 associated with the particular probe 20.

In operation, the test tone oscillator 30 operates in a manner substantially similar to a conventional astable multivibrator to provide a substantially square-wave AC signal having a predetermined frequency via the collectors of the transistors 96 and 98. The test tone signal provided at the collector of the transistor 98 is connected to the chopper transistor 136 of the modulator 32 via the signal path 18b. In response to the test tone signal connected thereto, the chopper transistor 136 controls the operation of the output transistors 138 and 140 so that the signal applied to the capacitor 148 varies between the positive amplitude level determined by the amplitude level of the signal applied to the collector of the output transistor 138 by the amplitude control transistor 134, and substantially circuit ground potential. The capacitor 148 and the resistor 154 cooperate to provide the probe drive signal via the signal path 18, the probe drive signal having the predetermined frequency and an amplitude which is determined by the amplitude control transistor 134.

The probe drive signal produced by the modulator 32 is then applied to the measurement contact 64 of the probe 14 via the signal path 18, the probe current sensor 16, and the second pole 168b of the switch assembly 168 interposed therein. As current flows from the modulator 32 through the probe 14 to the particulate material 22, the probe current sensor 16 operates to rectify the current and pass the rectified current through the ammeter 160 to thereby provide a visual indication of the current. Since the current is proportional to the conductivity of the particulate material 22, and the conductivity is proportional to the moisture content of the particulate material 22 it follows that the current indicator signal provided by the ammeter 160 is proportional to the mositure content of the particulate material 22.

In the preferred embodiment, the probe drive signal is also applied to the guard contact 68 via the signal path 18 and the guard voltage drop compensation assembly 90 interposed therein, the guard voltage drop compensation assembly 90 compensating for the voltage drop in the probe drive signal applied to the measurement contact 64 caused by the probe current sensor 16. As explained generally above, the effect of applying the probe drive signal to the guard contact 68 is to isolate the flow of current from the measurement contact 64 to the portion of the particulate material 22 lying between the measurement contact 64 and the relatively far portion 94 of the bin 24.

As explained generally above, the amplitude of the probe drive signal being applied by the measurement contact 64 to the particulate material 22 will vary according to the conductivity of the particulate material 22. Variations in the amplitude of the probe signal will be transmitted by the isolation amplifier 48 to provide the probe drive sense signal which has an amplitude proportional to the amplitude of the probe drive signal. At the same time, the calibration assembly 50 will be providing the reference signal which has an amplitude proportional to the amplitude of the test tone signal applied thereto by the test tone oscillator 30 via the signal path 36. The signal subtractor 52 will receive the probe drive sense signal and the reference signal, subtract the probe drive sense signal from the reference signal and provide the difference signal, the amplitude of which is effectively proportional to the amplitude deviation of the probe drive signal from the predetermined amplitude. The difference signal amplifier 54 will receive the difference signal provided by the signal subtractor 52 via the signal path 46, amplify the received difference signal, and apply the amplified difference signal to the demodulator 42 via the signal path 46.

The demodulator 42 demodulates the difference signal applied thereto to derive the portion of the difference signal which is in phase with the test tone signal. More particularly, the demodulator 42 operates to rectify the received difference signal in synchronization with the test tone signal applied thereto via the signal paths 36c and 36d, thereby effectively blanking out those components of the difference signal derived from sources other than the test tone oscillator 30. For example, the demodulator 42 operates to effectively remove from the difference signal any power supply induced hum and any deletrious oscillations induced by the components comprising the moisture indicator 10. The demodulated difference signal is then applied to the filter 44 via the signal path 60.

The filter 44 operates as an active element filter to smooth the demodulated difference signal by integration to produce the probe command signal. The probe command signal will have a DC amplitude substantially proportional to the amplitude deviation of the probe drive signal actually being applied to the particulate material 22 via the measurement contact 64, from the predetermined amplitude as determined by the amplitude of the reference signal provided by the calibration assembly 50. The probe command signal is then applied to the amplitude control transistor 134 of the modulator 32 via the signal path 38.

In response to the probe command signal, the amplitude control transistor 134 will vary the amplitude of the signal applied by the emitter thereof to the other elements comprising the modulator 32 to thereby vary the amplitude of the probe drive signal being produced on the signal path 18. In this manner, any variations in the amplitude of the probe drive signal being applied to the particulate material 22 via the probe 14 will be detected by the probe command signal generator 28 so that corrective action may be taken by the modulator 32.

Changes may be made in the construction and the arrangements of the parts or the elements of the preferred embodiment disclosed herein without departing from the spirit and scope of the invention as defined in the following claims.

What is claimed is:

1. An apparatus for providing an output indication proportional to the moisture content of particulate material, the apparatus comprising:

a signal generator providing a probe drive signal having a predetermined frequency and a predetermined amplitude;

a probe connected to the signal generator and having a portion contacting the particulate material, the probe receiving the probe drive signal and applying the probe drive signal to the particulate material;

feedback control means connected to the probe and to the signal generator, the feedback control means sensing deviations of the amplitude of the probe drive signal applied to the particulate material via the probe from the predetermined amplitude and modulating the amplitude of the probe drive signal provided via the signal generator to maintain the amplitude of the probe drive signal at the predetermined amplitude; and a probe current sensor interposed generally between the signal generator and the probe, the probe current sensor measuring the current flowing from the probe to the particulate material and providing a current indicator signal proportional to the measured current, the current indicator signal being proportional to the moisture content of the particulate material.

2. An apparatus for providing an output indication proportional to the moisture content of particulate material, the apparatus comprising:

a probe having a portion contacting the particulate material, the probe receiving a probe drive signal having a predetermined frequency and a predetermined amplitude and applying the probe drive signal to the particulate material;

a signal generator providing the probe drive signal, the signal generator comprising:

an oscillator providing a test tone signal having the predetermined frequency;

a modulator connected to the oscillator, the modulator receiving the test tone signal and a probe command signal, and modulating the amplitude of the received test tone signal in response to the received probe command signal to provide the probe drive signal; and a probe command signal generator connected to the oscillator, to the modulator and to the probe, the probe command signal generator receiving the test tone signal from the oscillator and the probe drive signal from the probe, and providing the probe command signal having an amplitude proportional to the amplitude deviation of the received probe drive signal from the predetermined amplitude; and a probe current sensor interposed generally between the signal generator and the probe, the probe current sensor measuring the current flowing from the probe to the particulate material and providing a current indicator signal proportional to the measured current, the current indicator signal being proportional to the moisture content of the particulate material.

3. The apparatus of claim 2 wherein the probe command signal generator is further defined to include:

a subtractor connected to the oscillator and to the probe, the subtractor receiving the test tone signal from the oscillator and the probe drive signal from the probe, subtracting the received probe drive signal from the received test tone signal, and providing a difference signal proportional to the amplitude deviation of the received probe drive signal from the predetermined amplitude;

a demodulator connected to the subtractor and to the oscillator, the demodulator receiving the difference signal and the test tone signal, and demodulating the received difference signal to derive the portion of the received difference signal which is in phase with the received test tone signal for output as a demodulated difference signal; and a filter connected to the demodulator and to the modulator, the filter receiving the demodulated difference signal and filtering the received demodulated difference signal to provide the probe command signal.

4. The apparatus of claim 3 wherein the subtractor is further defined to include:

an isolation amplifier connected to the probe, the isolation amplifier receiving the probe drive signal and providing a probe drive sense signal having an amplitude proportional to the amplitude of the received drive signal;

a calibration assembly connected to the oscillator, the calibration assembly receiving the test tone signal and providing a reference signal having an amplitude proportional to the amplitude of the received test tone signal the amplitude of the reference signal determining the predetermined amplitude of the probe drive signal; and a signal subtractor connected to the isolation amplifier, to the calibration assembly and to the demodulator, the signal subtractor receiving the probe drive sense signal and the reference signal, and subtracting the received probe drive sense signal from the received reference signal to provide the difference signal.

5. An apparatus for providing an output indication proportional to the moisture content of particulate material disposed in a metal bin, the apparatus comprising:

a signal generator providing a probe drive signal having a predetermined frequency and a predetermined amplitude;

a probe connected to the signal generator and having a portion contacting the particulate material, the probe receiving the probe drive signal and applying the probe drive signal to the particulate material, the probe comprising:

a measurement contact connected to the signal generator, the measurement contact being positioned inside the bin with at least a portion of the measurement contact contacting the particulate material; and a measurement contact insulator having a first portion interposed between the measurement contact and a predetermined portion of the bin, the first portion of the measurement contact insulator preventing the direct flow of current between the measurement contact and the predetermined portion of the bin; and a probe current sensor interposed between the signal generator and the measurement contact, the probe current sensor measuring the current flowing from the probe to the particulate material and providing a current indicator signal proportional to the measured current, the current indicator signal being proportional to the moisture content of the particulate material.

6. The apparatus of claim 5 wherein the probe is further defined to include:

a guard contact connected to the signal generator, the guard contact being interposed between the measurement contact insulator and the predetermined portion of the bin with at least a portion of the guard contact contacting the particulate material;

a guard contact insulator interposed between the guard contact and the predetermined portion of the bin, the guard contact insulator preventing the direct flow of current between the guard contact and the predetermined portion of the bin; and wherein the measurement contact insulator is further characterized as having a second portion interposed between the measurement contact and the guard contact, the second portion of the measurement contact insulator preventing the flow of current between the measurement contact and the guard contact.

7. An apparatus for providing an output indication proportional to the moisture content of particulate material disposed in a metal bin, the apparatus comprising:

a signal generator providing a probe drive signal having a predetermined frequency and a predetermined amplitude;

a probe connected to the signal generator and having a portion contacting the particulate material, the probe receiving the probe drive signal and applying the probe drive signal to the particulate material, the probe comprising:

a measurement contact connected to the signal generator, the measurement contact being positioned inside the bin with at least a portion of the measurement contact contacting the particulate material; and isolation means for isolating the flow of current from the measurement contact to a predetermined portion of the particulate material; and a probe current sensor interposed between the signal generator and the measurement contact, the probe current sensor measuring the current flowing from the probe to the particulate material and providing a current indicator signal proportional to the measured current, the current indicator signal being proportional to the moisture content of the particulate material.

8. The apparatus of claim 7 wherein the isolation means is further defined to include:

a guard contact connected to the signal generator, the guard contact being interposed between the measurement contact and a predetermined portion of the bin with at least a portion of the guard contact in contact with the particulate material;

a guard contact insulator interposed between the guard contact and the predetermined portion of the bin, the guard contact insulator preventing the direct flow of current between the guard contact and the predetermined portion of the bin; and a measurement contact insulator having a first portion interposed between the measurement contact and the predetermined portion of the bin and a second portion interposed between the measurement contact and the guard contact, the first portion of the measurement contact insulator preventing the direct flow of current between the measurement contact and the predetermined portion of the bin, and the second portion of the measurement contact insulator preventing the direct flow of current between the measurement contact and the guard contact.

9. Method for providing an output indication proportional to the moisture content of particulate material comprising the steps of:

generating a probe drive signal having a predetermined frequency and a predetermined amplitude;

applying the probe drive signal to the particulate material;

sensing deviations of the amplitude of the probe drive signal applied to the particulate material from the predetermined amplitude;

modulating the amplitude of the probe drive signal in response to the sensed deviations to maintain the amplitude of the probe drive signal at the predetermined amplitude;

measuring the current applied to the particulate material; and providing a current indicator signal proportional to the measured current, the current indicator signal being proportional to the moisture content of the particulate material.

10. Method for providing an output indication proportional to the moisture content of particulate material comprising the steps of:

generating a test tone signal having a predetermined frequency;

modulating the amplitude of the test tone signal in response to a probe command signal to provide a probe drive signal having the predetermined frequency and a predetermined amplitude;

applying the probe drive signal to the particulate material;

receiving the test tone signal and the probe drive signal applied to the particulate material and providing the probe command signal having an amplitude proportional to the amplitude deviation of the probe drive signal from the predetermined amplitude;

measuring the current applied to the particulate material; and providing a current indicator signal proportional to the measured current, the current indicator signal being proportional to the moisture content of the particulate material.

11. The method of claim 10 wherein the step of providing the probe command signal is further defined to include the steps of:

providing a difference signal proportional to the amplitude deviation of the probe drive signal from the predetermined amplitude;

demodulating the difference signal to derive the portion of the difference signal in phase with the test tone signal; and filtering the demodulated difference signal to provide the probe command signal.

12. The method of claim 11 wherein the step of providing the difference signal is further defined to include the steps of:

providing a probe drive sense signal having an amplitude proportional to the amplitude of the probe drive signal;

providing a reference signal having an amplitude proportional to the amplitude of the test tone signal the amplitude of the reference signal determining the predetermined amplitude of the probe drive signal; and subtracting the probe drive sense signal from the reference signal to provide the difference signal.

* * * * *